United States Patent [19]
Heras et al.

[11] Patent Number: 5,804,404
[45] Date of Patent: Sep. 8, 1998

[54] STABLE SUBSTRATE-CHROMOGEN SOLUTIONS FOR ENENZYME ACTIVITY DETECTION

[75] Inventors: Alfonso Heras, Goleta; Marc Key, Ojai, both of Calif.

[73] Assignee: Dako Corporation, Carpenteria, Calif.

[21] Appl. No.: 589,215

[22] Filed: Jan. 22, 1996

[51] Int. Cl.$^6$ .................................................. C12Q 1/28
[52] U.S. Cl. ................................. 435/28; 435/4; 435/25
[58] Field of Search .................................. 435/28, 975, 4, 435/25; 436/66

[56] References Cited

U.S. PATENT DOCUMENTS

| | | | |
|---|---|---|---|
| 4,596,770 | 6/1986 | Parham et al. | 435/7 |
| 4,615,912 | 10/1986 | Inoue et al. | 427/212 |
| 4,615,972 | 10/1986 | Gallacher | 435/28 |
| 4,755,472 | 7/1988 | Ismail et al. | 436/66 |
| 4,891,314 | 1/1990 | Pauly et al. | 435/28 |
| 5,006,461 | 4/1991 | Woiszwillo | 435/7.92 |
| 5,013,646 | 5/1991 | Woiszwillo | 435/7.92 |
| 5,206,150 | 4/1993 | Tai | 435/28 |

FOREIGN PATENT DOCUMENTS

| | | |
|---|---|---|
| 0271713 | 6/1988 | European Pat. Off. |
| 62-2294099 | 12/1987 | Japan |
| 62-294099 | 12/1987 | Japan |
| 5-227995 | 9/1993 | Japan |
| 6-165696 | 6/1994 | Japan |
| WO 85/02018 | 5/1985 | WIPO |
| WO 86/05207 | 9/1986 | WIPO |
| WO 90/02339 | 3/1990 | WIPO |

OTHER PUBLICATIONS

Brand et al., "Comparison of Particulate 3,3',5,5'–Tetramethylbenzidine and 3,3'–Diaminobenzidine as Chromogenic Substrates for Immunoblot," *Biotechniques*, 8(1):58–60, 1990.

Broyles et al., "Quantification of Small Amounts of Hemoglobin in Polyacrylamide Gels with Benzidine," *Analytical Biochemistry*, 94:211–219, 1979.

Conyers and Kidwell, "Chromogenic Substrates for Horseradish Peroxidase," *Analytical Biochemistry*, 192:207–211, 1991.

Liem et al., "Quantitative Determination of Hemoglobin and Cytochemical Staining for Peroxidase Using 3,3',5,5'–Tetramethylbenzidine Dihydrochloride, A Safe Substitute for Benzidine," *Analytical Biochemistry*, 98:388–393, 1979.

Morrel et al., "Comparison of Horseradish Peroxidase Visualization Methods: Quantitative Results and Further Technical Specifics," *J. Histochemistry and Cytochemistry*, 29(8):903–916, 1981.

Mesulam, "Tetramethyl Benzidine for Horseradish Peroxidase Neurohistochemistry: A Non–Carcinogenic Blue Reaction–Product with Superior Sensitivity for Visualizing Neural Afferents and Efferents," *J. Histochemistry and Cytochemistry*, 26(2):106–117, 1978.

*Primary Examiner*—John Kight
*Assistant Examiner*—Dameron Jones
*Attorney, Agent, or Firm*—Arnold, White, & Durkee

[57] ABSTRACT

The preparation and use of stable, ready-to-use substrate-chromogen solutions for the detection and quantification of peroxidase or pseudoperoxidase activity are described. The substrate-chromogen solution according to the present invention contains a buffer, preferably imidazole buffer, a polymer, a hydroperoxide substrate, a chromogenic organic electron donor and electron donor of the carbohydrate type as a stabilizer. The substrate-chromogen solution retains its full peroxidatic activity and develops a negligible color during storage.

29 Claims, 9 Drawing Sheets

STABLE SUBSTRATE-CHROMOGEN SOLUTIONS FOR ENENZYME ACTIVITY DETECTION

BACKGROUND OF THE INVENTION

I. Field of the Invention

This invention relates to the stabilization of ready-to-use substrate-chromogen solutions for determining peroxidase or pseudoperoxidase activity in an assay. In particular, this invention relates to the use of electron donors of the carbohydrate type that protect the substrate and chromogen from reacting in the absence of the catalytic enzyme.

II. Description of the Related Art

The detection of peroxidatic activity has broad application in analytical, biological and clinical chemistry. Many tests consists of exposing a mixture of a hydroperoxide and a chromogenic electron donor to a sample suspected of containing an analyte, the latter either being the catalyst or being associated with the catalyst. If the analyte is present, peroxidatic reaction will occur and a color characteristic of the chromogen used will be visible within a few seconds to a few hours.

Peroxidatic assays in which the analyte is the peroxidatic catalyst include those for detection of heme or hemoglobin in forensic specimens or in fluids, feces, urine, plasma or serum. Tests in which a peroxidase enzyme is attached to a molecule that directly or indirectly binds to the analyte include immunoassays, immunohistochemistry or nucleic acid hybridization. The detection of peroxidatic activity also is applicable to the localization of analytes bound to solid supports such as filters, cytological and histological sections, electrophoretic gels, or blots thereof.

Horseradish peroxidase (HRP) is a commonly used enzyme label for immunological or nucleic acid detection systems. In the presence of hydrogen peroxide ($H_2O_2$), the most common hydroperoxide used, HRP catalyzes the oxidation of phenols, naphthols, amines, diamines and numerous other compounds yielding chromogenic substances visible by light and electron microscopy, spectrophotometry or the naked eye. HRP decomposes two molecules of hydrogen peroxide into water and oxygen. This reaction is initiated when HRP donates a pair of electrons to hydrogen peroxide. The enzyme subsequently extracts electrons from a suitable chromogenic donor, which may form networks of polymers that remain in solution or as a precipitate, yielding characteristic soluble or insoluble pigments at the site of peroxidatic activity.

A consistent problem in chromogenic assays relying on peroxidatic activity has been the tendency of hydroperoxides and chromogenic electron donors to spontaneously react before the addition of the catalytic enzyme. This spontaneous oxidation, also described as "background," limits the usable time of indicator solutions often to no more than a few hours. It is well known that one of the factors contributing to this oxidation is contamination of the chromogen solutions with trace amounts of oxidizing agents such as transition metals.

Because of this spontaneous reaction, the general practice is to mix the hydroperoxide and the chromogenic electron donor immediately before use. Mesulam, *J. Histochem. Cytochem.*, 26:106–117 (1978), described the spontaneous oxidation of TMB and suggested as essential the use of containers free of oxidizing agents. Morrel et al., *J. Histochem. Cytochem.*, 29:903–916 (1981) noted that if labware was not adequately cleaned, TMB solutions turn blue before addition of $H_2O_2$. Broyles et al., *Anal. Biochem.*, 94:211–219 (1979), reported that benzidine-$H_2O_2$ solutions should be used within two hours of preparation, turning brown if stored overnight, even at 4° C. Liem et al., *Anal. Biochem.*, 98:388–393 (1979), point out that TMB has good staining properties, but also that its solubility is low and that TMB is subject to oxidative decomposition. Brand et al., *Biotechniques*, 8:58–60 (1990) compared the stability of DAB and TMB using immunoblots and concluded that the TMB was functional for eight weeks with visible precipitates after 19 hours at room temperature and DAB was functional for four weeks with precipitates forming after 18 hours at room temperature. These precipitates are an indication of polymerization due to spontaneous oxidation.

Of the different substrate-chromogens for peroxidase, only TMB has been reported to be stable for long periods of time as a single reagent. Different references have disclosed various technologies to stabilize substrate-chromogens for peroxidase, mainly by the use of: (1) cyclodextrins (gamma-cyclodextrin JP 06,165,696 and Beta-cyclodextrin WO 8,605,207); (2) surfactants (cationic JP 05,227,995 and non-ionic JP 62,294,099); (3) antibiotics (Bacitracin U.S. Pat. No. 5,206,150 and Penicillin U.S. Pat. No. 4,891,314); (4) polymers (U.S. Pat. No. 5,013,646 and U.S. Pat. No. 4,615,972); and (5) chelators (EP 0271,713 and WO 9,002, 339). It is evident that there remains a definite need for a versatile, environmentally safe and inexpensive technology to stabilize ready-to-use substrate-chromogen solutions for HRP enzyme assays.

SUMMARY OF THE INVENTION

It is, therefore, an object of the present invention to provide formulations for stabilizing substrate-chromogen aqueous compositions for the visual, calorimetric, spectrophotometric or reflectometric indication of peroxidatic or psuedoperoxidatic activity. It also is an object to provide methods for the use of such stabilizing compositions. Such compositions save storage space by eliminating the need to have separate containers of individual reagents and save time by avoiding the need to mix the individual reagents at the time of the test. They also provide improved sensitivity and reproducibility in such assays.

In satisfying these objects, there is provided a composition comprising a buffer having a pH of between about 3 and 8, a hydroperoxide, a chromogenic electron donor and an electron donor of the carbohydrate type. The carbohydrate is selected from a wide group of mono-, di- or polysaccharides effective at inhibiting spontaneous oxidation of chromogenic electron donors. In addition, a polymer may be included in the composition.

In a preferred embodiment, chromogenic electron donors TMB and AEC are dissolved in the solvent 1-methyl-2-pyrrolidone (M2P) and diluted to the desired final concentration to form a first solution. The advantages of this solvent are increased solubility of the chromogen and decreased expense and toxicity when compared to organic solvents. Alternatively, hydrochloride salts of other chromogenic electron donors like DAB and OPD can be easily dissolved in an aqueous buffer.

A second buffered solution also contains a carbohydrate compound which can be selected from a wide range of related, non-oxidized compounds. Examples include glyceraldehyde, erythrose, threose, deoxyribose, ribose, arabinose, fructose, xylose, lyxose, allose, altrose, glucose, mannose, gulose, idose, galactose, talose, cellobiose, maltose, sucrose, lactose, xylobiose, raffinose, melezitose and cellulose. In addition, a hydroperoxide, either in liquid or solid form, is also included in the second solution. Commercially available hydroperoxides include hydrogen peroxide, urea hydrogen peroxide and the tertiary alkyl hydroperoxides, t-butyl hydroperoxides and cumene hydroperoxide. In addition, a chelator or chelators as described in EP 0 271 713 WO 90/02339) can be added to the second solution in order to increase the stability of the substrate-chromogen solution. The polymer, if included, is added as part of the second solution.

The first solution and second carbohydrate solutions are thoroughly mixed together to form a third solution. The third solution may be sterilized, for example by filtering. The stabilized substrate-chromogen solution is then ready to be used in a peroxidatic assay. The presence of the carbohydrate, which acts as a stabilizer of the substrate-chromogen solution, permits storage of the third solution until it is ready to be used. Recommended storage conditions are in a dark, e.g., amber bottle at 2° C. to 8° C.

DETAILED DESCRIPTION OF THE PREFERRED EMBODIMENTS

Figure 1:
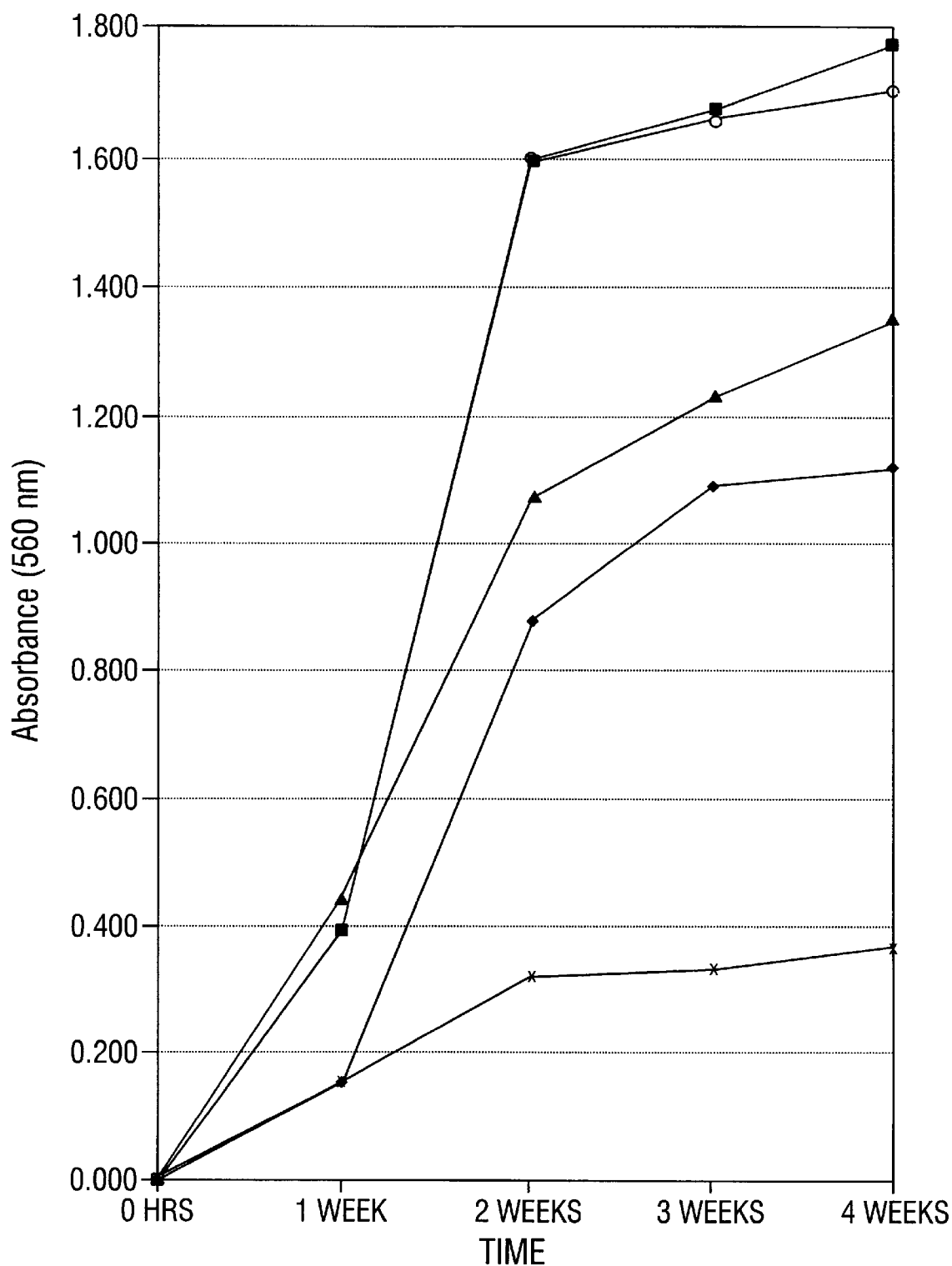
FIG. 1—Spontaneous Oxidation of DAB in Various Buffers. acetate (♦); citrate (■) phosphate (▲); imidazole (X); tris (○).

The present invention permits the economical preparation of stable liquid formulations for assays involving peroxidatic and pseudoperoxidatic activity. The solutions contain both a hydroperoxide and a chromogenic electron donor and, unlike previous formulations, retain full peroxidatic activity while developing negligible color during long term storage. This is a major advance over the prior art formulations which are plagued by spontaneous reaction of the chromogen after even short periods of time.

I. Definitions

"Peroxidatic activity" refers to the ability of catalytic substances to drive the reaction of hydroperoxides with colorless chromogenic electron donors which become fluorescent or visibly colored after oxidation. The peroxidatic activity may be measured as follows. For AEC and DAB, peroxidase-conjugated streptavidin (1 mg/ml) is diluted 1:1600 in ultrapure water and further diluted 1:10 with the substrate-chromogen solution to be tested to give a final dilution of the peroxidase conjugate of 1:16,000. This is easily accomplished by using a 96-well plate to mix 90 $\mu$l of the substrate-chromogen with 10 $\mu$l of the diluted peroxidase conjugate. The mixture is incubated at room temperature for ten minutes and read spectrophotometrically at 560 nm without stopping the reaction. For OPD and TMB, the peroxidase conjugated streptavidin is diluted 1:512,000 in ultrapure water and then mixed 1:10 with the substrate-chromogen solution (10 $\mu$l of peroxidase and 90 $\mu$l of substrate-chromogen) to give a final dilution of the peroxidase conjugate of 1:5,120,000. Incubation is at room temperature for 15 minutes and the reaction is stopped by adding 50 $\mu$l of 1N $H_2SO_4$. Readings are taken at 405 nm for OPD and 450 nm for TMB. The true peroxidatic activity is obtained by subtracting the spontaneous oxidation or background from the spectrophotometric readings obtained.

"Pseudoperoxidatic activity" refers to the ability of an endogenous peroxidase or a non-peroxidase catalytic substance to drive the reaction of hydroperoxidases with colorless chromogenic electron donors which become fluorescent or visibly colored after oxidation. Certain transition metals and their ions and hemoproteins are known to have pseudoperoxidatic activity. Basophils, neutrophils, eosinophils and mast cells synthesize endogenous peroxidase which can be visualized at the ultrastructural level in the secretory apparatus of immature cells. Red blood cells and hematin containing compounds have iron as part of their heme groups, which can catalyze the oxidation of chromogenic electron donors. This pseudoperoxidatic activity can be inhibited with strong $H_2O_2$ solutions, sodium azide and methanol-$H_2O_2$ solutions.

"Peroxidatic assay" refers to any test or procedure that is based on a peroxidatic activity, as defined above, to generate a signal which can be detected or measured to evidence the presence of analyte or the amount present.

"Spontaneous oxidation" refers to the spontaneous production of visible color of a chromogenic electron donor in the absence of peroxidase enzyme. This is measured for AEC and DAB by reading the absorbance of 100 $\mu$l of the substrate-chromogen at 560 nm. For OPD and TMB, this is accomplished by mixing 100 $\mu$l of the substrate-chromogen with 50 $\mu$l of 1N $H_2SO_4$, then reading at 405 nm for OPD and 450 nm for TMB.

"Chromogenic electron donor" refers to a compound which undergoes an easily observed change in color upon oxidation by an oxidizing agent such as a hydroperoxide. Examples of these are: benzidine, 3,3'-dimethylbenzidine (o-tolidine, OTD), 3,3'-dimethoxybenzidine (o-dianisidine, oDAD), 3,3'-diaminobenzidine (DAB), 3,3',5,5'-tetramethylbenzidine (TMB), 3,3'-diethylbenzidine, 2,7-diaminofluorene (DAF), o-phenylenediamine (OPD), N,N-diethylphenylenediamine (DEPDA), N,N-dimethylphenylenediamine (DMPDA), 2,2'-azino-di (3-ethyl-benzthiazoline sulfonate) (ABTS), 3-methyl-2-benzothiazolinone hydrazone hydrochloride (MBTH), aminoethyl carbazole (AEC), and 4-chloro-1-naphthol (4-CN).

"Hydroperoxide" refers to compounds of the general formula, ROOH, wherein the R group is an aryl, alkyl, or acyl group (organic hydroperoxide), or hydrogen atom (hydrogen peroxide). If R is the formula, $R_1R_2R_3$ where $R_1$, $R_2$ and $R_3$ is any combination of aryl and alkyl groups other than hydrogen, the hydroperoxide is a tertiary alkyl hydroperoxide. If $R_1$ is a phenyl group and $R_2$ and $R_3$ are methyl groups, the hydroperoxide is cumene hydroperoxide. If $R_1$, $R_2$ and $R_3$ are methyl groups, the hydroperoxide is tertiary butyl hydroperoxide.

"Storage lifetime" of a substrate-chromogen solution is the time interval after initial preparation of the indicator solution in which (a) the absorbance of said solution in the 400–800 nm wavelength range remains below 0.05 and (b) the peroxidatic activity of said solution is at least about 80% of its initial value.

II. Catalysts for Peroxidatic Activity

The catalysts for peroxidatic oxidation are derived from five main classes: i) certain transition-metal ions and their complex ions, ii) hematin compounds, iii) hemoproteins, iv) the peroxidase enzymes and v) the catalase enzymes. A hydroperoxidase also can react with itself to produce molecular oxygen and the corresponding alcohol. This reaction is catalyzed by the same classes of compounds that catalyze peroxidatic reactions. Many of the electron donors for peroxidatic reactions also can be oxidized by molecular oxygen. These oxidation reactions also tend to be catalyzed by transition metal ions. The most common transition metals frequently found as contaminants in chemical reagents that can catalyze a measurable reaction between hydroperoxides and chromogenic electron donors are Cr, Mn, Fe, Ni and Co. See WO 90/02339.

III. Preparation of the Chromogen, Reaction and Final Solutions

This invention relates to an innovative and novel technology to stabilize substrate-chromogenic formulations for assaying peroxidatic or pseudoperoxidatic activity. A chromogen solution, referred to hereafter as "the first solution," contains a chromogen susceptible to peroxidatic oxidation in a suitable solvent or buffer. The buffered substrate solution contains a buffer of pH between about 3 and 8, preferably imidazole or a combination of other buffers with imidazole, a hydroperoxide and an electron donor of the carbohydrate type and, optionally, a polymer. This solution is referred to hereafter as "the second solution." Upon mixing of these solution to form a "third solution," the chromogen remains stable despite the presence of the hydroperoxide.

Although various peroxidatic catalysts can be assayed over a broad pH, most assays, especially those that use HRP, are performed optimally in the pH 4–6 range. Imidazole-HCl is the preferred buffer because of its ability to promote solubilization of most chromogenic electron donors, when combined with polymers, and also because of its excellent buffer capacity between pH 5.0 and 7.8. Moreover, imidazole has been demonstrated to enhance peroxidatic activity of OPD and DAB. Imidazole can be used alone or combined with other buffers at a concentration between 1 and 500 mM, preferably 50 mM.

Polymers are molecules of high molecular weight that are formed from repeating subunits of simpler molecules. Many polymers are formed from compounds that contain carbon-carbon double bonds by a process that is called addition polymerization. The addition of polymers to the buffered substrate solution increases the solubility and also reduces the spontaneous oxidation of the chromogenic electron donor. Preferred polymers are polyethylene glycol (PEG) or propylene glycol (PG), employed at a concentration between 1 and 1000 mM.

Because of their unlimited aqueous solubility and relative non-toxicity, preferred hydroperoxides in this invention are hydrogen peroxide and urea hydrogen peroxide at a concentration between 0.1 and 10 mM. In addition, they are much more sensitive to peroxidatic catalysts than alkyl hydroperoxides or peroxyacids.

Examples of the chromogenic electron donors covered by this invention are: benzidine, 3,3'-dimethylbenzidine (o-tolidine, OTD), 3,3'-dimethoxybenzidine (o-dianisidine; oDAD), 3,3'diaminobenzidine (DAB), 3,3',5,5'tetramethylbenzidine (TMB), 3,3'diethylbenzidine, 2,7-diaminofluorene (DAF), o-phenylenediamine (OPD), N,N-diethylphenylenediamine (DEPDA), N,N-dimethylphenylenediamine (DMPDA), 2,2'-azino-di (3-ethyl-benzthiazoline sulfonate (ABTS), 3-methyl-2-benzothiazolinone hydrazone hydrochloride (MBTH), aminoethyl carbazole (AEC), and 4-chloro-1-naphthol (4-CN). Different chromogens have individual solubilities which are pH dependent. Practically, their concentrations should not exceed their solubilities. Some chromogens need organic solvents to be initially solubilized, mainly dimethylsulfoxide (DMSO), N,N-dimethylformamide (DMF), 1-methyl-2-pyrrolidone (M2P) or methanol. In the preferred embodiment, AEC and TMB stocks are dissolved in M2P. AEC is dissolved in M2P at a concentration between 100 and 200 mM, preferably 150 mM. TMB is dissolved at a concentration between 10 and 150 mM, preferably 30 mM. Hydrochloride salts of other chromogens like DAB and OPD can be easily dissolved directly into the aqueous buffer. Preferred final concentration of a given chromogen electron donor is between 1 and 20 mM.

The electron donor of the carbohydrate type, used to stabilize the substrate-chromogen solutions, can be selected from a wide range of non-oxidized related compounds. Examples of these are glyceraldehyde, erythrose, threose, deoxyribose, ribose, arabinose, fructose, xylose, lyxose, allose, altrose, glucose, mannose, gulose, idose, galactose, talose, cellobiose, maltose, sucrose, lactose, raffinose, xylobiose, melezitose and cellulose. Monosaccharides are preferred because they are more active at lower concentrations. The optimal concentration of the electron donor will depend on the chromogenic electron donor used. Ideal concentrations of the carbohydrate selected may range from 0.01 mM to 1M.

The chromogen solution and the buffer, polymer, hydroperoxide and carbohydrate solution, prepared at room temperature, are thoroughly mixed together, filter sterilized with a 0.2 μm filter and placed in an amber bottle at 2° C. to 8° C. The stabilized substrate-chromogen solution is then ready for storage or for use in a peroxidatic assay.

IV. Formats and Reaction Conditions

An analyte-specific binding assay is an analytical procedure for detecting and/or quantitating a particular analyte which can be recognized by a second binding moiety, which is not expected to bind to any other substance in the test. This binding moiety substance is directly or indirectly linked to a signal-generating moiety, which is an enzyme. For the purpose of the present invention, the enzyme must be peroxidase, preferably from horseradish root, or a catalase enzyme. If the analyte is an antigen and the detection substance is an antibody, or vice-versa, the enzyme-linked analyte specific binding assay is known as "enzyme immunoassay' (EIA) or "enzyme-linked immunosorbent assay" (ELISA). If the analyte is an antigen or antibody attached to a cell or a tissue structure in a cytological or histological sample and the binding moiety is an antibody or antigen specific for the analyte, the peroxidase linked analyte-specific binding assay is known as an "immunoperoxidase cytochemical or histochemical staining". If the analyte is an antigen or antibody which has been captured on or in a solid support, and the binding moiety is an antibody or antigen specific for the analyte, where the enzyme-generated signal is visualized in the solid support, the analyte-specific binding assay is known as "immunoblot", "immuno dot blot", or "Western blot", depending on how capture occurs. If the analyte is a specific sequence of DNA or RNA and the binding moiety is a nucleic acid probe or a peptide nucleic acid (PNA), containing a base sequence complementary to at least a part of the analyte sequence, the analyte-specific binding assay is known as "nucleic-acid hybridization". If the nucleic acid has been captured on a solid support and the enzyme-generated signal is expected to remain on the support at the point of generation, the nucleic acid procedure is known as "nucleic acid dot blot hybridization", or as "Southern or Northern blot", depending on how capture occurs and on whether the analyte is DNA or RNA. If the nucleic acid analyte is part of a cytochemical smear or a histological section, the nucleic acid or PNA procedure is known as "in situ nucleic acid hybridization assay".

V. Kits

"Test kit" refers to any combination of equipment, reagents, and/or instructions for the use of equipment and/or reagents to assay for the presence or quantitation of an analyte. Examples include test kits for performing peroxidase based analyte-specific binding assays such as EIA, ELISA, immunoperoxidase cytochemical or histochemical staining, nucleic acid hybridization assays, and assaying the "pseudoperoxidatic activity" of blood or hemoglobin in forensic or clinical test samples.

Kits of the present invention, will also typically include a means for containing the equipment, reagents and/or instructions in close confinement for commercial sale, i.e., injection or blow-molded plastic containers in which the desired reagent is retained. Other containers suitable for conducting certain steps of the disclosed methods may also be provided.

VI. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Effect of Different Buffers on the Spontaneous Oxidation of DAB

Using ultrapure water, 50 mM solutions at pH 6.0 were prepared for the following buffers: acetate, citrate, phosphate, imidazole and tris. 7.5 mM PEG (MW 3,350), 2.77 mM DAB-4HCl and 2.94 mM $H_2O_2$ were added to each of the buffers, completely mixed, filter sterilized and stored at 4° C. protected from light. The spontaneous oxidation rate was measured once a week for one month at 560 nm using an ELISA reader.

FIG. 1 shows the effect of different buffers on the spontaneous oxidation of DAB. Imidazole buffer gave the best results with lower oxidation rates and no precipitates after 4 weeks at 4° C. Acetate and phosphate buffers had 3 and 3.7 times the oxidation rate of imidazole and some precipitates after 3 weeks. Citrate and Tris buffers had the highest oxidation rate plus visible amount of precipitates after 2 weeks.

Example 2

Effect of Different Carbohydrates on the Oxidation and Perocidatic Activity of DAB Using a 50 mM imidazole buffer at pH 6.0 containing 7.5 mM PEG, 2.94 mM $H_2O_2$, and 2.77 mM of DAB-4HCl as a base, the following carbohydrates were added at 10 mM: no carbohydrates, galactose, glucose, fructose, ribose and xylose. The DAB solution was filter sterilized, stored at 4° C. and protected from light. Spontaneous oxidation and peroxidatic activity were measured at 560 nm once a week for one month.

Figure 2:
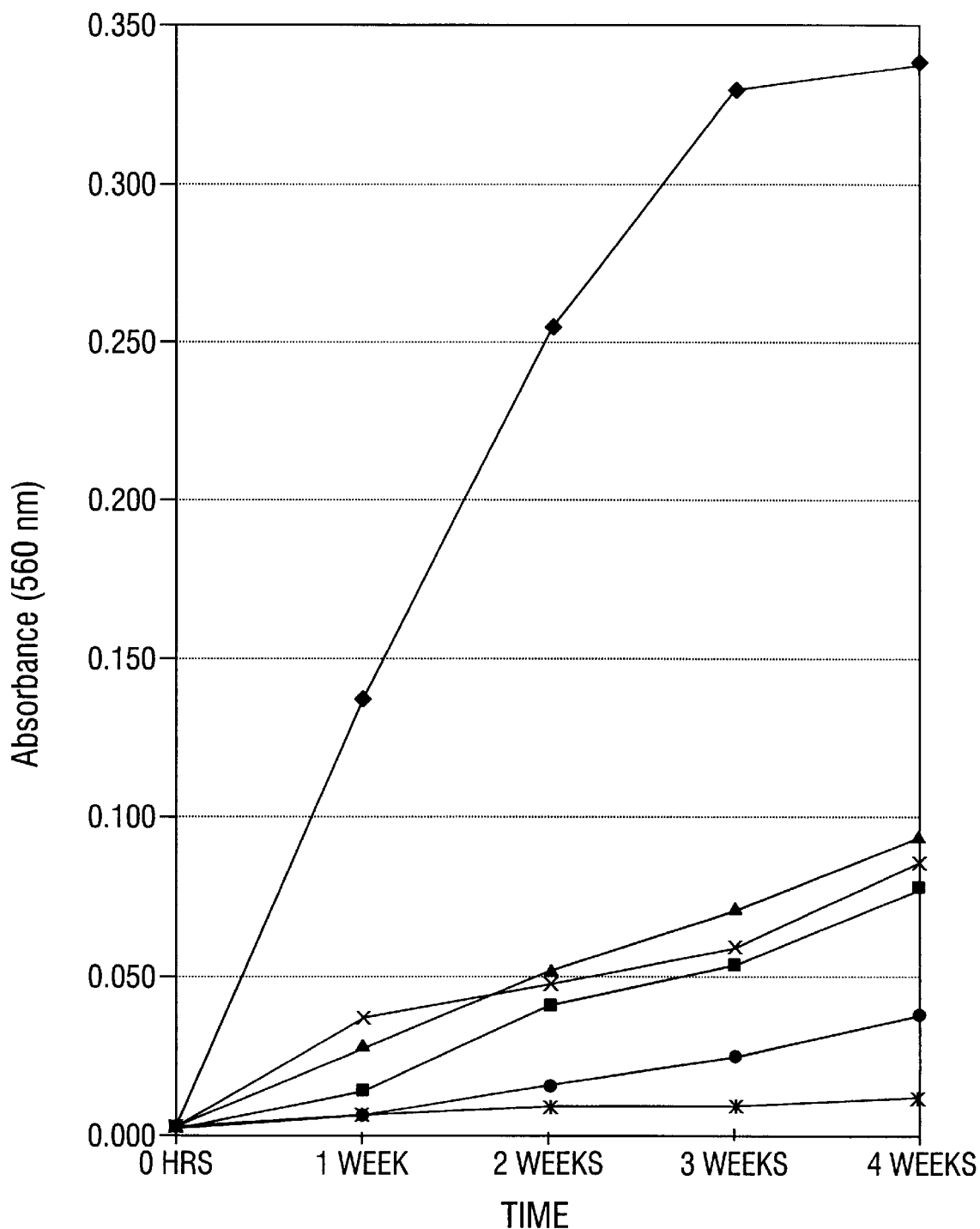
FIG. 2—Carbohydrate Effect on Spontaneous Oxidation of DAB. No carbohydrates (♦); galactose (■); glucose (▲); fructose (X); ribose; xylose (●).

FIG. 2, shows the effect of different carbohydrates on the spontaneous oxidation of DAB. Ribose and xylose had the lowest oxidation rates, followed by galactose, fructose and glucose which had an average of 7 times more the oxidation than ribose after 4 weeks at 4° C. The DAB substrate-chromogen solution with no carbohydrates visibly oxidized faster than the solutions containing carbohydrates.

Figure 3:
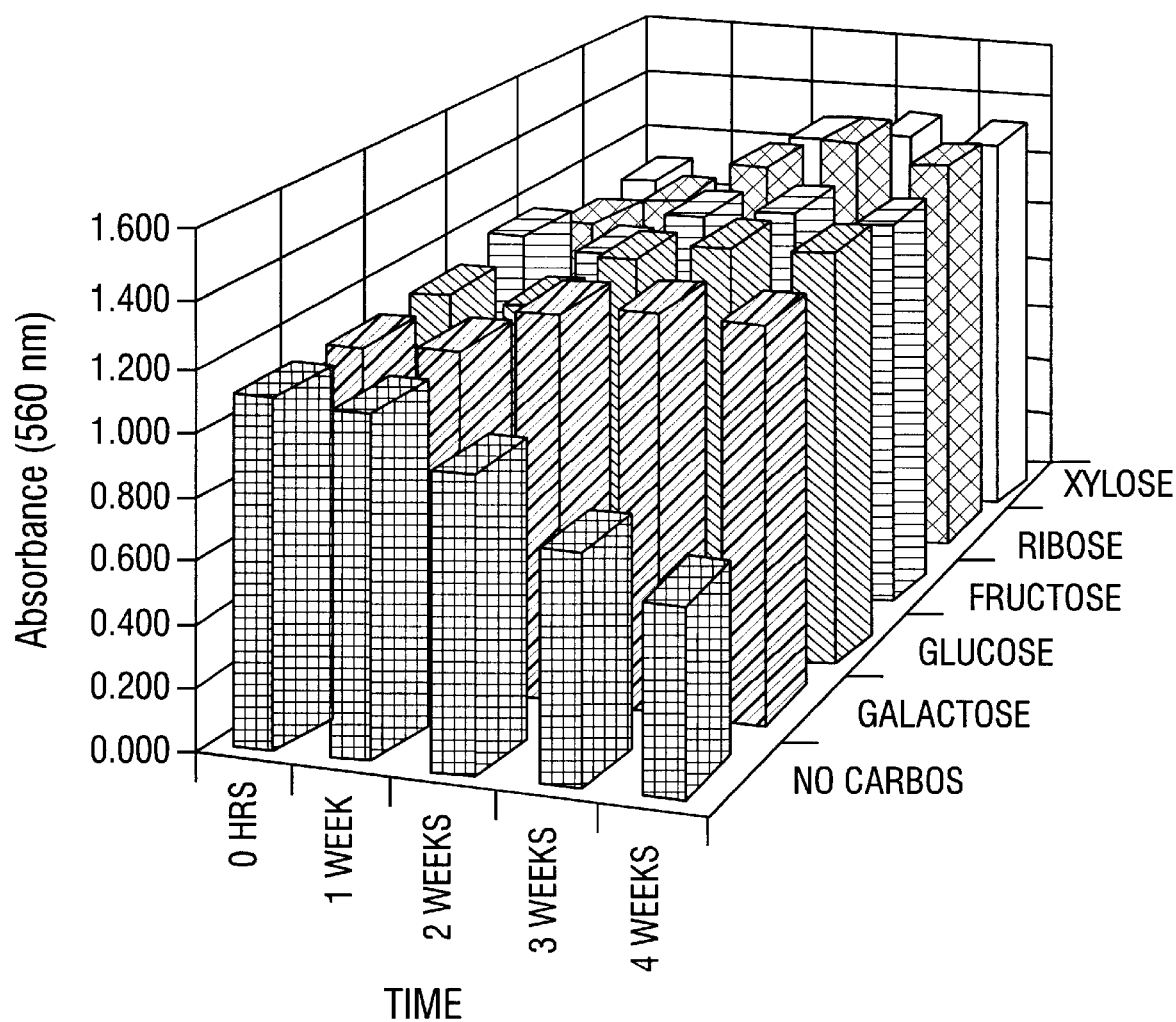
FIG. 3—Carbohydrate Effect on Spontaneous Oxidation of DAB (three dimensional).

FIG. 3, shows the effect of different carbohydrates on the peroxidatic activity of DAB. All the DAB solutions containing galactose, glucose, fructose, ribose, or xylose had 100% of their peroxidatic activity after 4 weeks at 4° C. The DAB solution without carbohydrates had 54.7% of peroxidatic activity after 4 weeks at 4° C.

Example 3

Effect of Glucose on the Oxidation and Peroxidatic Activity of AEC

A 50 mM Acetate buffer pH 5.0 containing 7.5 mM PEG, 2.94 mM $H_2O_2$ and 3.56 mM of AEC was used with or without 5 mM of glucose. The AEC was added from a 145 mM stock in M2P. The AEC solution was filter sterilized, and stored at 4° C. protected from light. Spontaneous oxidation and peroxidatic activity were measured at 560 nm once a week for one month.

Figure 4:
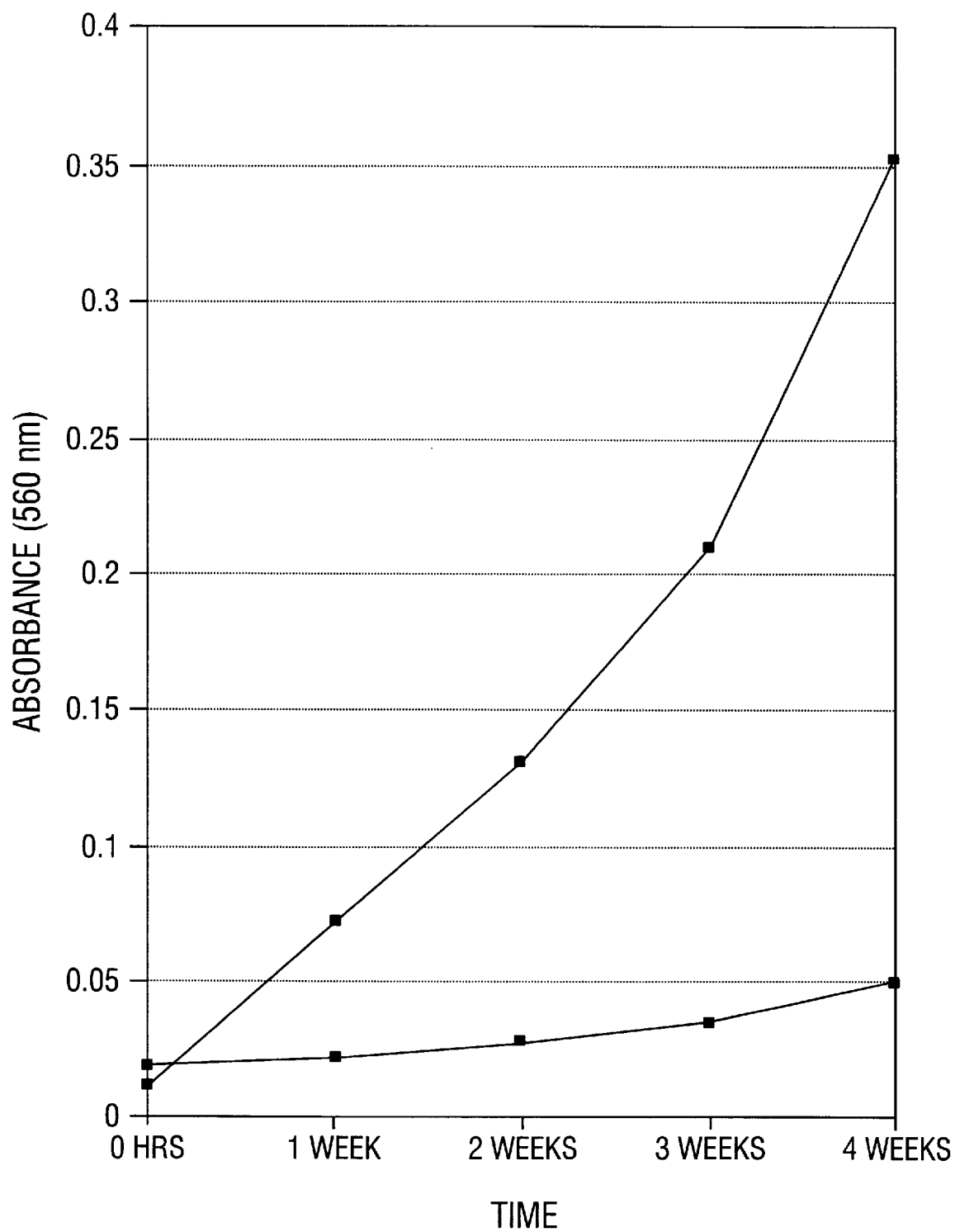
FIG. 4—Glucose Effect on Spontaneous Oxidation of AEC. No carbohydrates (♦); glucose (■).

FIG. 4 shows the effect of glucose on the spontaneous oxidation of AEC. The AEC solution containing 5 mM of glucose had less oxidation than the control solution without glucose, which was visibly oxidized and had some precipitates. The AEC solution without glucose had 7 times more the oxidation rate of the solution containing glucose.

Figure 5:
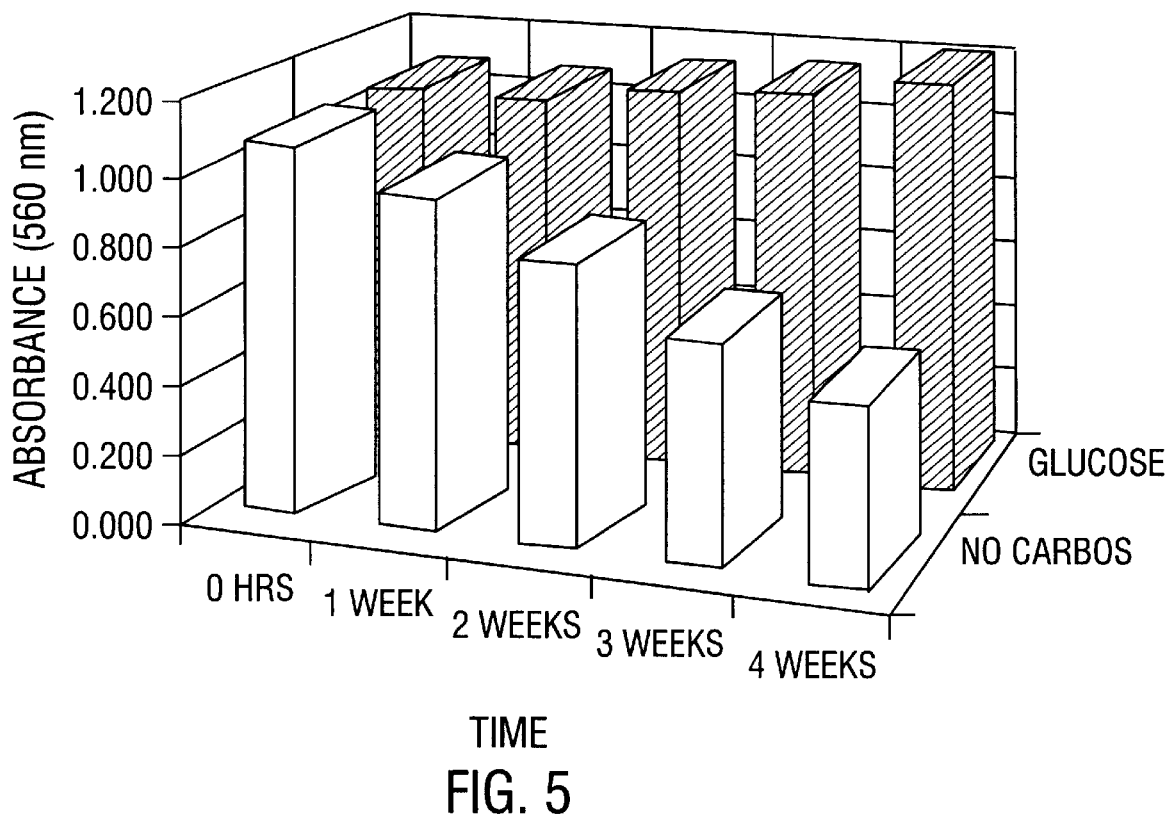
FIG. 5—Glucose Effect on Spontaneous Oxidation of AEC (three dimensional).

FIG. 5 shows the effect of glucose on the peroxidatic activity of AEC. The AEC substrate-chromogen solution with 5mM glucose retained its full peroxidatic activity after 4 weeks at 4° C., whereas the solution without glucose lost 53.6% of its original activity.

Example 4

Effect of Different Carbohydrates on the Oxidation and Peroxidatic Acitvity of OPD A 50 mM Imidazole buffer pH 5.0 containing 7.5 mM PEG, 2.94 mM $H_2O_2$ and 3.59 of OPD was used and the following carbohydrates were added: no carbohydrates, glucose 25 mM, ribose 2.5 mM and xylose 10 mM. The OPD solution filter sterilized and stored at 4° C. protected from light. Spontaneous oxidation and peroxidatic activity were measured at 492 nm once a week for a month.

Figure 6:
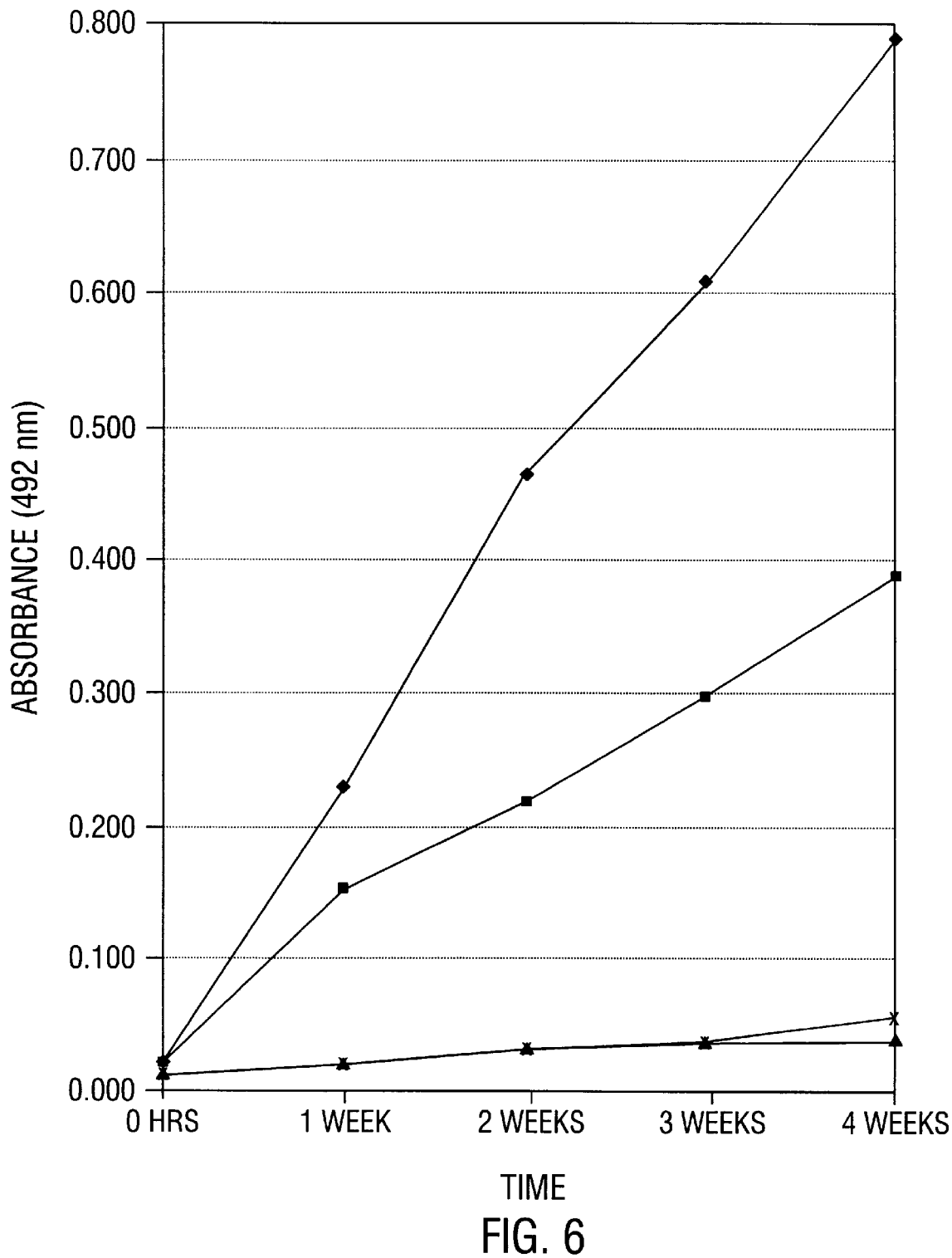
FIG. 6—Carbohydrate Effect on Spontaneous Oxidation of OPD. No carbohydrate (♦); glucose (■); ribose (▲); xylose (X).

FIG. 6 depicts the effect of different carbohydrates on the spontaneous oxidation of OPD. Ribose and xylose had the lowest oxidation rates, followed by glucose which had 9 times more oxidation than ribose after 4 weeks at 4° C. The OPD substrate-chromogen solution with no carbohydrates visibly oxidized faster than the solutions containing carbohydrates with 19 times more oxidation than ribose and some precipitates after 3 weeks at 4° C.

Figure 7:
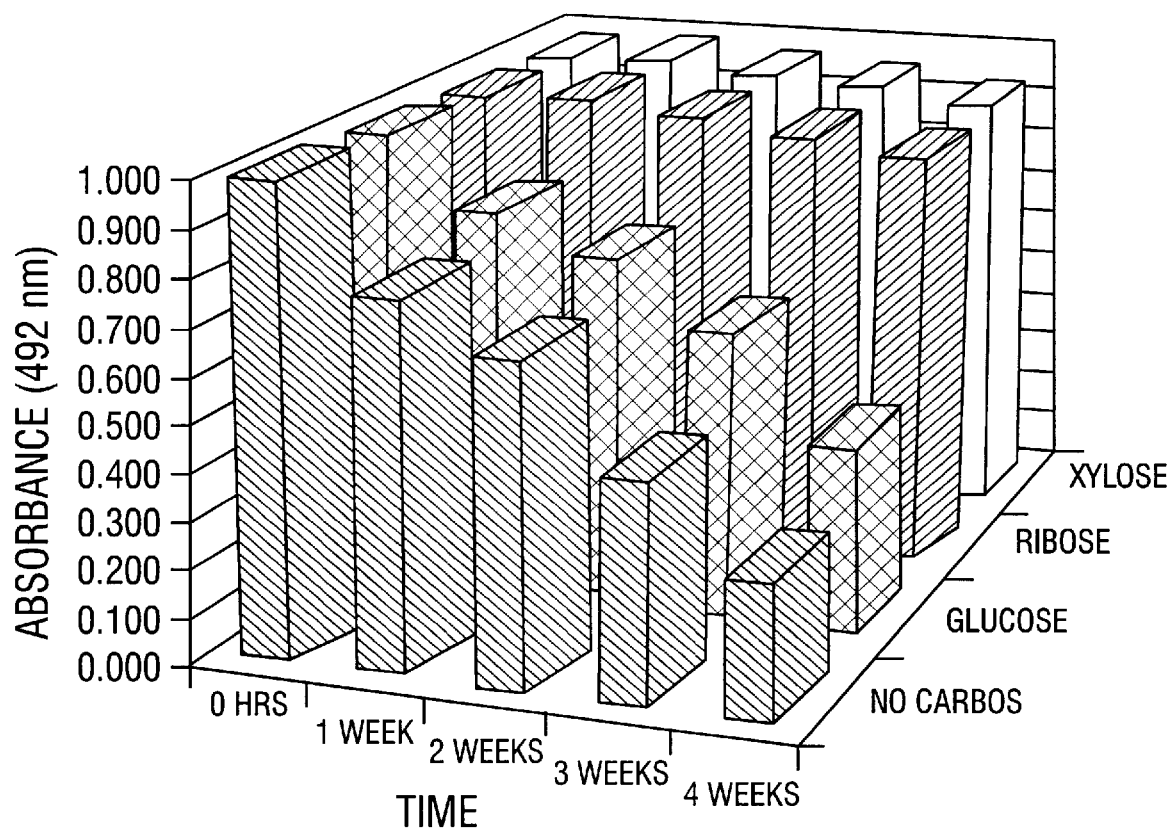
FIG. 7—Carbohydrate Effect on Spontaneous Oxidation of OPD (three dimensional).

FIG. 7 shows the effect of different carbohydrates on the peroxidatic activity of OPD. The OPD substrate-chromogen solutions containing xylose had 95 % and ribose had 92% of their peroxidatic activity after 4 weeks at 4° C. The solution with glucose had 41 % and no carbohydrates had 28% of peroxidatic activity after 4 weeks at 4° C.

Example 5

Effect of Different Carbohydrates on the Oxidation and Peroxidatic Acitivty of TMB A 50 mM Imidazole buffer pH 5.0 containing 7.5 mM PEG, 2.94 mM $H_2O_2$ and 1.60 mM of TMB was used and the following carbohydrates were added: no carbohydrates, glucose 100 mM, ribose 50 mM and xylose 75 mM. The TMB was added from a 31.91 mM stock in M2P. The TMB solution was filter sterilized and stored at 4° C. protected from light. Spontaneous oxidation and peroxidatic activity were measured at 450 nm once a week for one month.

Figure 8:
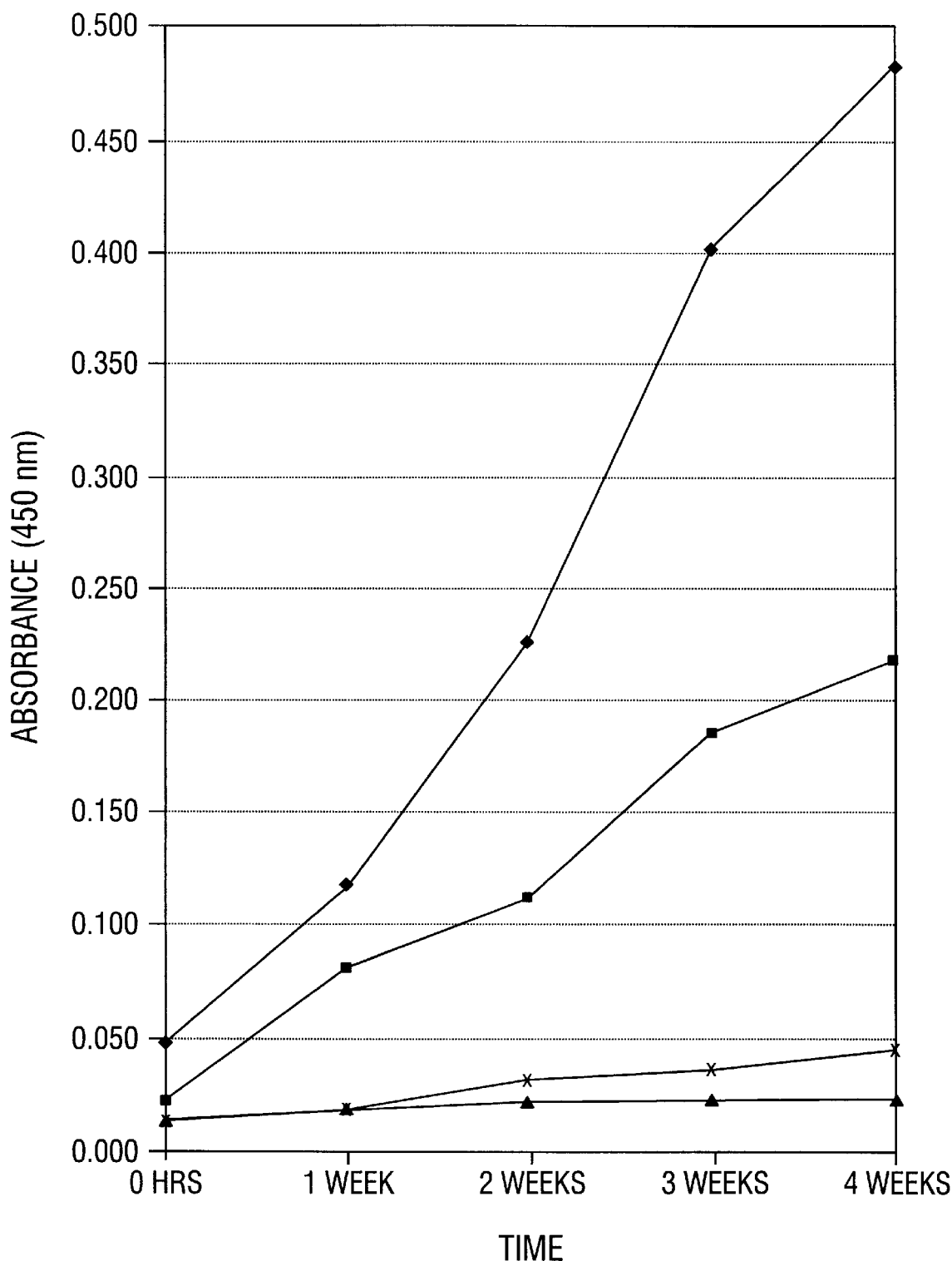
FIG. 8—Carbohydrate Effect on Spontaneous Oxidation of TMB. No carbohydrates (♦); glucose (■); ribose (▲); xylose (X).

FIG. 8 depicts the effect of different carbohydrates on the spontaneous oxidation of TMB. Ribose and xylose had the lowest oxidation rates, followed by glucose which had 9 times more oxidation than ribose after 4 weeks at 4° C. The TMB substrate-chromogen solution with no carbohydrates visibly oxidized faster than the solutions containing carbohydrates with 20 times more oxidation than ribose and some precipitates after 3 weeks at 4° C.

Figure 9:
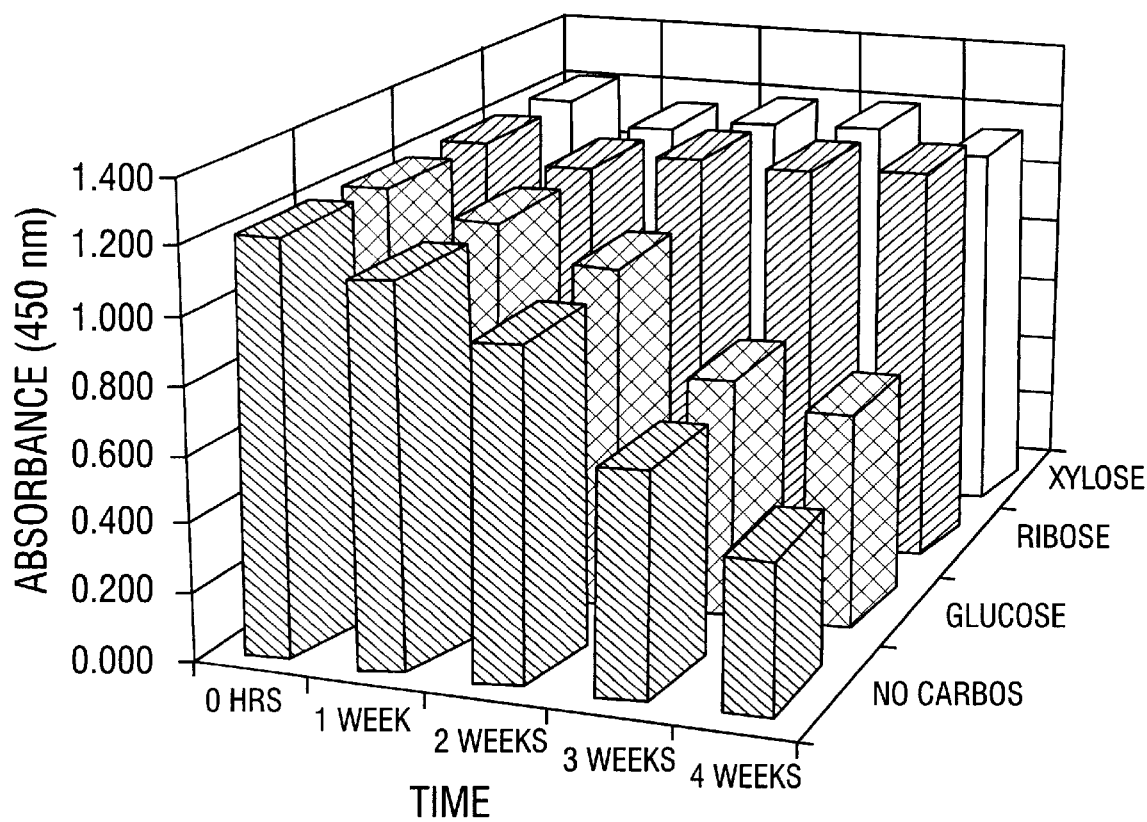
FIG. 9—Carbohydrate Effect on Spontaneous Oxidation of TMB (three dimensional).

FIG. 9 shows the effect of different carbohydrates on the peroxidatic activity of TMB. The TMB substrate-chromogen solution containing ribose had 100% of its peroxidatic activity after 4 weeks at 4° C. The solution with xylose had 93%, glucose had 54% and no carbohydrates had 36% of peroxidatic activity after 4 weeks at 4° C.

What is claimed is:

1. A composition for the detection and measurement of peroxidatic activity comprising:
    (i) a chromogenic electron donor,
    (ii) a hydroperoxide,
    (iii) an aqueous buffer, and
    (iv) a reducing carbohydrate stabilizing agent.

2. The composition according to claim 1, wherein said chromogenic electron donor is DAB, OPD, AEC or TMB.

3. The composition according to claim 2, wherein said chromogenic electron donor is AEC or TMB dissolved in a water-miscible organic solvent selected from the group consisting of DMSO, DMF, methanol or 1-methyl-2-pyrrolidone.

4. The composition according to claim 2, wherein the final concentration of said chromogenic electron donors is between about 0.1 mM and 20 mM.

5. The composition according to claim 1, wherein said hydroperoxide is hydrogen peroxide or urea hydrogen peroxide.

6. The composition according to claim 1, wherein the concentration of said hydroperoxide is between about 0.1 mM and 10 mM.

7. The composition according to claim 1, wherein said aqueous buffer has a pH of between about 3.0 and 8.0.

8. The composition according to claim 1, wherein the aqueous buffer is imidazole hydrochloride buffer or a mixture thereof.

9. The composition according to claim 8, wherein the concentration of said buffer is between about 1 mM and 500 mM.

10. The composition according to claim 9, wherein the concentration is 50 mM.

11. The composition according to claim 1, wherein said formulation further comprises a polymer.

12. The composition according to claim 11, wherein said polymer is polyethylene glycol or propyleneglycol.

13. The composition according to claim 12, wherein the concentration of said polymer is between about 1 mM and 1000 mM.

14. The composition according to claim 1, wherein said carbohydrate stabilizing agent is a monosaccharide, a disaccharide or a polysaccharide.

15. The composition according to claim 1, wherein the final concentration of said carbohydrate is between 0.01 mM and 1 M.

16. A method of assaying for peroxidatic activity in a sample comprising the steps of:
    (i) providing a composition comprising (a) a chromogenic electron donor, (b) a hydroperoxide, (c) an aqueous buffer, and (d) a reducing carbohydrate as stabilizing agent;
    (ii) contacting said composition with a sample; and
    (iii) measuring the pigmented form of said chromogenic electron donor.

17. A method for the preparation of a formulation in claim 1, comprising the following steps:
    (i) forming a first solution by dissolving a chromogenic electron donor in a solvent;
    (ii) forming a second solution by preparing a buffer containing a polymer, a hydroperoxide substrate and a stabilizing agent of the carbohydrate type; and
    (iii) forming a third solution by mixing said first and said second solutions.

18. The method of claim 17, wherein said solvent is water miscible and said buffer is acidic.

19. The method of claim 17, further comprising the step of filter sterilization of said third solution.

20. The method of claim 19, further comprising protecting said filter sterilized third solution under light protective conditions.

21. The method of claim 20, further comprising storage of the filter sterilized third solution at room or refrigeration temperatures.

22. A kit comprising:
    (i) a chromogenic electron donor,
    (ii) a hydroperoxide,
    (iii) an aqueous buffer, and
    (iv) a reducing carbohydrate as stabilizing agent.

23. The kit according to claim 22, wherein said chromogenic electron donor is DAB, OPD, AEC or TMB.

24. The kit according to claim 23, wherein said chromogenic electron donor is AEC or TMB dissolved in a water-miscible organic solvent for selected from the group consisting of DMSO, DMF, methanol or 1-methyl-2-pyrrolidone.

25. The kit according to claim 24, wherein said hydroperoxide is hydrogen peroxide or urea hydrogen peroxide.

26. The kit according to claim 22, wherein the aqueous buffer is imidazole hydrochloride buffer or a mixture thereof.

27. The kit according to claim 22, wherein said formulation further comprises a polymer.

28. The kit according to claim 23, wherein said polymer is polyethylene glycol or propyleneglycol.

29. A method for formulating an improved chromogenic electron donor solution, the improvement comprising:
 (i) forming a first solution by dissolving a chromogenic electron donor in a solvent;
 (ii) forming a second solution by preparing a buffer containing a polymer, a hydroperoxide substrate and a stabilizing agent of the reducing carbohydrate type; and
 (iii) forming a third solution by mixing said first and said second solutions.

* * * * *

UNITED STATES PATENT AND TRADEMARK OFFICE
CERTIFICATE OF CORRECTION

PATENT NO.    :   5,804,404

DATED         :   September 8, 1998

INVENTOR(S)   :   Alfonso Heras and Marc Key

It is certified that error appears in the above-identified patent and that said Letters Patent is hereby corrected as shown below:

Title page, item # "[54]", line 2, delete "ENENZYME" and substitute ---ENZYME-- therefor , and col. 1, line 2.
Title page, item # "[73]", delete "Carpenteria" and substitute ---Carpinteria--therefor.

Signed and Sealed this

Nineteenth Day of January, 1999

Attest:

Attesting Officer

*Acting Commissioner of Patents and Trademarks*